(12) United States Patent
Cartier et al.

(10) Patent No.: US 7,959,619 B2
(45) Date of Patent: Jun. 14, 2011

(54) HYGIENE PANTS FOR SINGLE USE

(75) Inventors: Jean-Francois Cartier, Drummondville (CA); Christian Dumas, Drummondville (CA); Hans Een, Molnlycke (SE); Marcus Lehto, Gothenburg (SE); Lucas Back, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 291 days.

(21) Appl. No.: 11/441,160

(22) Filed: May 26, 2006

(65) Prior Publication Data

US 2006/0271009 A1 Nov. 30, 2006

Related U.S. Application Data

(63) Continuation-in-part of application No. PCT/SE2005/000319, filed on Mar. 2, 2005.

(51) Int. Cl.
A61F 13/15 (2006.01)
A61F 13/20 (2006.01)

(52) U.S. Cl. ........... 604/385.01; 604/358; 604/385.3; 604/385.24

(58) Field of Classification Search .......... 604/358, 604/385.01, 385.03, 385.3, 385.22, 385.24, 604/385.25, 385.27, 385.31, 396; 2/401
See application file for complete search history.

(56) References Cited

U.S. PATENT DOCUMENTS 3,424,162 A * 1/1969 Parravicini .......... 604/396
3,629,027 A 12/1971 Germain
3,701,710 A 10/1972 Germaine et al.
5,236,430 A 8/1993 Bridges
5,440,764 A 8/1995 Matsushita
(Continued)

FOREIGN PATENT DOCUMENTS

EP 0 234 658 A1 9/1987
(Continued)

OTHER PUBLICATIONS

Copending U.S. Appl. No. 11/847,765, filed Aug. 30, 2007, entitled "Hygiene Pants for Single Use," Publication No. 2008/0021430 A1.

(Continued)

*Primary Examiner* — Tatyana Zalukaeva
*Assistant Examiner* — Susan Su
(74) *Attorney, Agent, or Firm* — Buchanan Ingersoll & Rooney PC

(57) ABSTRACT

Disposable hygiene pants with a front portion (2), a rear portion (3) and a crotch portion (4) provided with two leg openings (5, 6), the longitudinal edge portions (21, 22) of the front portion being connected by longitudinal weld seams (7, 8) to the longitudinal edge portions (31, 32) of the rear portion (3) in order to form a waist opening (9) and two leg openings (5, 6) in the crotch portion, which leg openings are outwardly delimited in the transverse direction by the inner end portions of the weld seams as seen in the longitudinal direction of the hygiene pants. The hygiene pants have an outer cover (10) and comprise an absorption unit (11). The cover is preferably made of an elastic laminate. The weld seams (7, 8) are each reinforced by at least one reinforcing strip (15, 16) containing thermoplastic fibers and have a tensile strength, in a direction transverse to the weld seam, in excess of 5 N/25.4 mm at least in the portions reinforced with said nonwoven strip (15, 16).

37 Claims, 7 Drawing Sheets

U.S. PATENT DOCUMENTS

| | | | |
|---|---|---|---|
| 5,591,298 A | | 1/1997 | Goodman et al. |
| 5,628,738 A | | 5/1997 | Suekane |
| 5,682,618 A | * | 11/1997 | Johnson et al. .................. 2/275 |
| 5,746,730 A | | 5/1998 | Suzuki et al. |
| 5,769,838 A | | 6/1998 | Buell et al. |
| 5,772,825 A | * | 6/1998 | Schmitz ..................... 156/164 |
| 5,779,831 A | | 7/1998 | Schmitz |
| 5,895,382 A | * | 4/1999 | Popp et al. ............... 604/385.21 |
| 5,931,827 A | * | 8/1999 | Buell et al. ............... 604/385.29 |
| 6,042,673 A | | 3/2000 | Johnson et al. |
| 6,120,487 A | * | 9/2000 | Ashton ................... 604/385.29 |
| 6,240,569 B1 | * | 6/2001 | Van Gompel et al. ............ 2/400 |
| 6,258,077 B1 | * | 7/2001 | Buell et al. .................... 604/393 |
| 6,476,289 B1 | | 11/2002 | Buell et al. |
| 6,585,713 B1 | | 7/2003 | LeMahieu et al. |
| 6,635,135 B2 | | 10/2003 | Kuen et al. |
| 6,652,501 B2 | | 11/2003 | Malchow et al. |
| 6,716,778 B1 | | 4/2004 | Hottner |
| 6,773,527 B2 | | 8/2004 | Campbell et al. |
| 6,837,961 B2 | | 1/2005 | Malchow et al. |
| 6,840,930 B1 | * | 1/2005 | Miyamoto et al. ....... 604/385.31 |
| 7,047,572 B2 | | 5/2006 | Hopkins |
| 7,582,077 B2 | * | 9/2009 | Otsubo ....................... 604/391 |
| 7,621,900 B2 | * | 11/2009 | Van Gompel et al. ... 604/385.24 |
| 2003/0022582 A1 | | 1/2003 | Cree et al. |
| 2003/0065295 A1 | | 4/2003 | Malchow et al. |
| 2003/0069554 A1 | | 4/2003 | Malchow et al. |
| 2003/0120252 A1 | | 6/2003 | Franke et al. |
| 2004/0102757 A1 | | 5/2004 | Olson |
| 2004/0243086 A1 | | 12/2004 | Vangompel et al. |
| 2005/0137563 A1 | * | 6/2005 | Van Gompel et al. ... 604/385.27 |
| 2006/0271009 A1 | | 11/2006 | Cartier et al. |
| 2007/0233034 A1 | | 10/2007 | Hildeberg et al. |
| 2007/0255246 A1 | * | 11/2007 | Schneider ................ 604/385.31 |
| 2007/0293833 A1 | | 12/2007 | Wennerback |
| 2008/0021430 A1 | | 1/2008 | Back |
| 2008/0033387 A1 | | 2/2008 | Wastlund-Karlsson et al. |
| 2008/0108964 A1 | | 5/2008 | Edwall |

FOREIGN PATENT DOCUMENTS

| | | |
|---|---|---|
| EP | 0 625 346 A1 | 5/1994 |
| EP | 0 625 346 A | 11/1994 |
| EP | 0 875 226 A2 | 11/1998 |
| EP | 0 990 434 A2 | 4/2000 |
| EP | 1 077 055 A2 | 2/2001 |
| EP | 1 247 507 A2 | 10/2002 |
| EP | 1 491 105 A1 | 12/2004 |
| FR | 2 873 545 A1 | 2/2006 |
| JP | 05-015552 A | 1/1993 |
| JP | 9-506004 A | 6/1997 |
| JP | 10 043235 A | 2/1998 |
| JP | 2005-511345 A | 4/2005 |
| WO | WO 94/01069 A1 | 1/1994 |
| WO | WO 99/27876 A1 | 6/1999 |
| WO | WO 02/17843 A2 | 3/2002 |
| WO | WO 03/047488 A1 | 6/2003 |
| WO | WO 03/057469 A1 | 7/2003 |
| WO | WO 03/086258 A1 | 10/2003 |
| WO | WO 2005/122984 A1 | 12/2005 |
| WO | WO 2005/122985 A1 | 12/2005 |
| WO | WO 2006/004637 A1 | 1/2006 |
| WO | WO 2006/038837 A1 | 4/2006 |
| WO | WO 2006/093444 A1 | 9/2006 |
| WO | WO 2007/133127 A1 | 11/2007 |
| WO | WO 2007/133128 A1 | 11/2007 |

OTHER PUBLICATIONS

Office Action dated Sep. 9, 2008 in Copending U.S. Appl. No. 12/007,662, filed Jan. 14, 2008.

Back, Copending U.S. Appl. No. 11/847,765, filed Aug. 30, 2007, entitled "Hygiene Pants for Single Use".

Edwall et al., Copending U.S. Appl. No. 12/007,662, filed Jan. 14, 2008, entitled "Absorbent Article".

Norrby, Copending U.S. Appl. No. 12/279,211, filed Oct. 15, 2008, entitled "Method of Reinforcing a Bond Between Web Materials and an Absorbent Article Comprising Bonded Web Materials".

Russian Office Action dated Aug. 28, 2009 issued in Russian Federation Application No. 2008136900/14(047345).

Office Action dated Jun. 12, 2009 in Copending U.S. Appl. No. 11/847,765, filed Aug. 30, 2007.

Office Action dated Oct. 12, 2010, issued in Japanese Patent Application No. 2008-521350, and English translation thereof.

\* cited by examiner

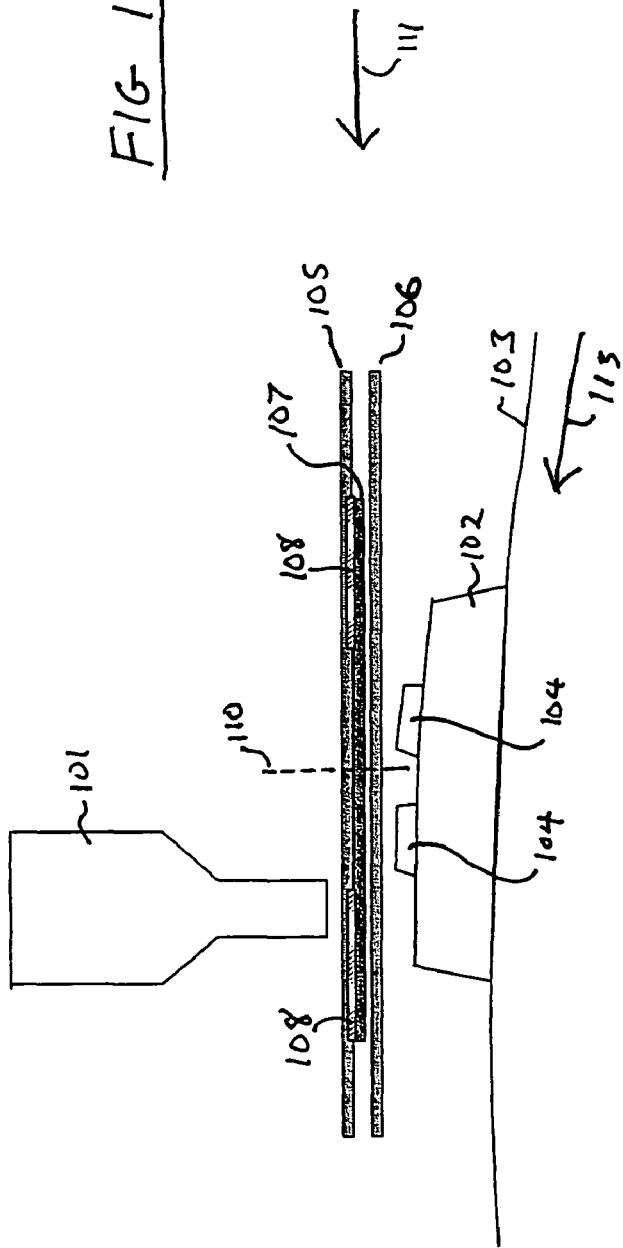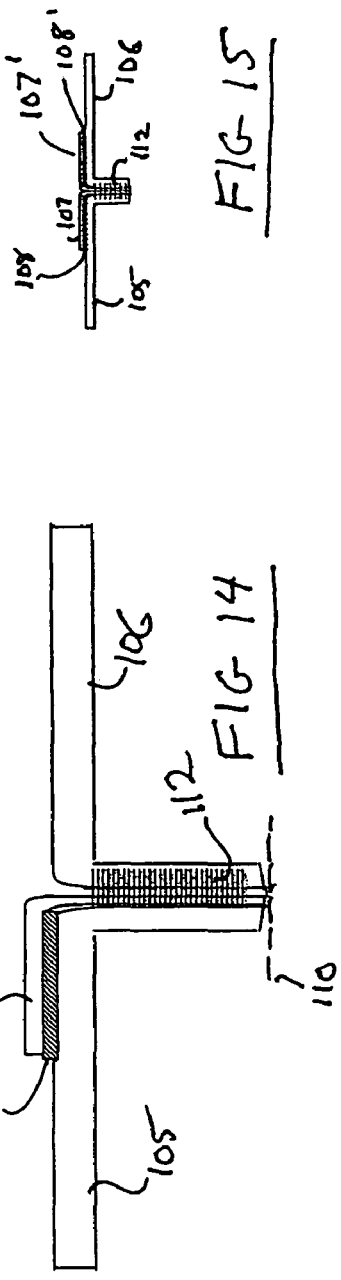

HYGIENE PANTS FOR SINGLE USE

TECHNICAL FIELD

The present invention relates to disposable hygiene pants, such as diaper pants.

BACKGROUND

Very high demands are placed on fit and comfort for hygiene pants such as diaper pants for children and sanitary towel pants for adults. The hygiene pants preferably have sufficient elasticity in the transverse direction (i.e., the horizontal direction when the pants are held upright) that they are easy to take off and put on by the user, a parent or a care provider. There is also a preference that they should be soft and textile-like. Hygiene pants, in particular for adult users, are preferably discrete and not bulky, at least in the areas outside the actual absorption unit. Since they are disposable products, the cost is preferably minimized, in particular the costs of materials and manufacture. For cost reasons, the material layers included are preferably as thin as possible. At the same time, quality and strength requirements must be fulfilled.

Hygiene pants, such as diaper pants, preferably resist wear and breakage during use. Hygiene pants can be placed under significant stresses when being put on, for example the pants are stretched when they are being pulled over the user's hips. In particular, longitudinal weld seams connecting front portions to back portions of the garment at the sides of the pant are exposed to considerable stresses.

In traditional hygiene pants, covers have been made of double nonwoven layers with elastic threads lying between these. In welded side seams on this type of cover, there are no fewer than four layers of bonded nonwoven, in which the bonds have not been broken open or weakened in connection with the production of the cover, which can provide a sufficiently strong weld seam.

WO 03/047488 discloses an elastic laminate composed of an elastic film applied between two nonwoven layers. During production of the elastic laminate, these nonwoven layers have been connected to the film, after which the laminate has been stretched until bonds in the nonwoven layer have been broken. As a result, the elasticity of the laminate is largely the same as the elasticity of the elastic film. One disadvantage of this solution is that weld seams in hygiene pants constructed with covers made of such laminates can have considerably less strength than the weld seams on traditional diaper pants.

Other examples of elastic laminates used in construction of hygiene pants are described in PCT applications WO 2005/122984 and WO 2005/122985. In contrast to the production method disclosed in WO 03/047488, the bonds of at least one nonwoven layer have not been completely broken, instead, the layer retains a certain residual strength. PCT applications WO 2005/122984 and WO 2005/122985 describe laminates in which elasticity has been combined with softness and resistance to puncture. However, welded side seams of hygiene pants constructed of laminates described in PCT applications WO 2005/122984 and WO 2005/122985 can still be weaker that the weld seams of traditional pants.

As can be seen from the above, many demands, some of them contradictory, are placed on disposable hygiene pants. Improvements in the art are still to be desired.

SUMMARY

Described herein are disposable hygiene pants, such as diaper pants. The pants can be described with reference to a longitudinal direction, which corresponds to the vertical when the pants are held upright, and a transverse direction, which is a horizontal direction from side to side as the pants are held upright. The pants comprise in the longitudinal direction, a front portion, an intermediate crotch portion provided with leg opening cutouts, and a rear portion, the outer longitudinal edge portions of the front portion being connected by longitudinal weld seams to the outer longitudinal edge portions of the rear portion in order to form a waist opening delimited by the outer transverse edge portions of the front portion and of the rear portion and forming two leg openings in the crotch portion, said leg openings being delimited in the transverse direction by inner end portions of the weld seams. The hygiene pants comprise an absorption unit extending in the longitudinal direction across at least part of the crotch portion. The hygiene pants also comprise an outer cover that is preferably made of elasticized material, for example elastic material comprising an elastic film applied to a layer of nonwoven material or a layer of elastic film applied between two layers of nonwoven material.

The pants comprise weld reinforcing pieces of material that comprise thermoplastic fibers, such as bonded nonwoven material, applied to each longitudinal edge portion of at least one of said front portion and said back portion such that a portion of a weld reinforcing piece of material extends into each of said weld seams between said longitudinal edge portions of said front portion and said back portion. In preferred embodiments, the reinforcing material is bonded nonwoven material.

Weld reinforcing pieces of material can be adhesively affixed to the inner surface of the front and/or back portions of the elastic laminate outer cover. Preferably the reinforcing material is affixed to the cover by adhesive that is applied proximate to the weld, and most preferably the adhesive is positioned such that it is proximate to the weld seam, but does not extend into the area of the weld seam. As used herein, proximate to the weld seam means close to the weld seam, for example within at least about 5 cm, preferably at least within about 3 cm and most preferably at least in a location within about 1 cm of the weld. Generally, it is preferred to place the adhesive as close as practical to the location of the weld seam without extending into the weld seam, but this is not to exclude the reinforcing material also being affixed by adhesive that is less proximate to the weld seam, for example in the case of a piece of reinforcing material that extends transversely across either the front or back portion adhesive may be used continuously or at discrete points across the width of the reinforcing strip. Additional pieces of reinforcing nonwoven material may be applied so as to extend into each weld with or without being adhesively affixed.

Accordingly, in preferred embodiments the weld seams are each reinforced by at least one strip of material containing thermoplastic fibers, which has been applied to said longitudinal edge portions of the front portion and rear portion of the hygiene pants at least along said inner end portions, as seen in the longitudinal direction of the hygiene pants, of the two edge portions and has been welded together with said longitudinal edge portions of the cover in order to form said weld seams. A reinforcing strip can be as narrow as the weld, but is preferably sufficiently wide in the transverse direction to accommodate being adhesively affixed near the weld, preferably such that the adhesive is not applied in the area where the weld is formed. The reinforcing strip may span the transverse width of the pant on the front and or back portions, such a strip can be adhesively affixed to either the front or back portion using adhesive at a location proximate to the weld and the strip may also be adhesively affixed at points that are less proximate to the weld seam.

The hygiene pants are preferably reinforced in the weld seams as described above such that the tensile strength of the weld seams, in a direction transverse to the weld seam, exceeds 5 N/25.4 mm, more preferably the minimum tensile strength exceeds 10 N/25.4 mm or 12 N/25.4 mm and can be on average at least 15 N/25.4 mm or 20 N/25.4 mm in the portions reinforced with said nonwoven strip. The breaking strength of the cover in the transverse direction preferably exceeds the tensile strength for the reinforced weld seams.

According to one embodiment, the longitudinal edge portions of both the front portion and the rear portion of the cover, at least along the inner end portions thereof, in the vicinity of the waist opening of the pant and/or in the vicinity of the leg opening, can comprise reinforcing strips.

The weld seams of the hygiene pants can comprise, at least in their reinforced areas, two layers of said reinforcing strips. In one embodiment, a reinforcing strip is adhesively affixed to the cover proximate to the weld seams in each of said longitudinal edge portions of either the front portion or the rear portion, and in that a reinforcing strip is applied with or without adhesive to each longitudinal edge portion of the other of the front portion or the rear portion.

In some embodiments, wherein when the weld seam is made, either the front or the back portion is disposed toward an ultrasonic horn and the other of the front or back portion is disposed toward an anvil, reinforcing strips of nonwoven material are affixed on the inner surface of the portion that is disposed toward the ultrasonic horn. In some embodiments in which this arrangement is preferred, when the weld seam is being made, the ultrasonic horn is stationary with respect to the transverse direction of the pant and the anvil is moving in the transverse direction of the pant. Alternatively, where the reinforced weld is weaker between the front portion and the reinforcing strip or between the back portion and the reinforcing strip, the reinforcing strip is preferably adhesively affixed proximate to the weld seam on whichever of the front or back portion is on the weaker side.

In some embodiments, the reinforcing bonded material is composed of a single strip extending transversely across the hygiene pants. The reinforcing material can extend in the longitudinal direction for the length the weld seam. Alternatively, in the longitudinal direction of the hygiene pants, a strip can extend only across the inner and/or outer longitudinal end portions of the two transverse edge portions.

In another aspect, an improved method of forming a weld seam between a first material, and a second material, preferably elastic materials such as an elastic laminate. The method comprises adhesively adhering a reinforcing bonded nonwoven material comprising thermoplastic fibers to at least one of said first and second materials proximate to the location of the weld such that a potion of said reinforcing material extends into the location of the weld seam between said first and second materials. In preferred embodiments, the adhesive is placed such that it is proximate to, but not in the area of the weld seam. In particularly preferred embodiments, where the weld seam is formed along a longitudinal direction between materials that are moving in a transverse direction by using a stationary ultrasonic horn and an anvil moving or rotating in the transverse direction at a rate equivalent to the first and second materials such that said first material is disposed toward the horn and the second material is disposed toward the anvil as the weld is being formed, the reinforcing material is adhesively adhered to at least the first material. Alternatively, where the reinforced weld seam is weaker between the first material and the reinforcing material, or between the second material and the reinforcing material, the reinforcing material is preferably adhesively affixed to whichever of the first or second materials is on the weaker side.

DESCRIPTION OF THE FIGURES

FIGS. 13-15 illustrate a method of making a reinforced weld seam between layers of elastic laminate according to a preferred embodiment.

DETAILED DESCRIPTION OF PREFERRED EMBODIMENTS

Elastic laminates have various desirable attributes when used as elastic covers for hygiene pants. A laminate comprising an elastic film between two nonwoven layers can give the cover desired elastic properties while the fibers in these nonwoven layers give the cover a soft textile feel. The structure of the laminate is preferably configured such that elastic stretching of the cover is not impeded by the nonwoven layers. However, the strength of weld seams of hygiene pants having elastic laminate covers can be adversely affected by the structure and make-up of the laminate, in which the fiber bonds have been partially or completely broken. In some elastic laminate cover materials, the fibers of the nonwoven layers have been more or less stretched to the breaking point in the manufacture of the laminate.

It has also been discovered that typical methods of constructing weld seams such as used in hygiene pants can affect the strength of the weld seams in surprisingly adverse ways. In particular it has been discovered that in a high-speed production line using a stationary ultrasonic horn and a transversely moving anvil to form a weld along a longitudinal direction, the weld may be significantly weaker, and that when the weld involves more than two layers the weld between layers on the horn side tend to be weaker. Without wishing to be bound by theory, it is believed that this phenomenon can be explained by the breakage of fibers in the transversely moving material while in contact with the stationary horn.

By means of the methods described herein, the risk of welded side seams in hygiene pants prematurely breaking can be significantly reduced, so that elastic laminate materials can be safely and economically used to construct improved hygiene pants.

Figure 1:
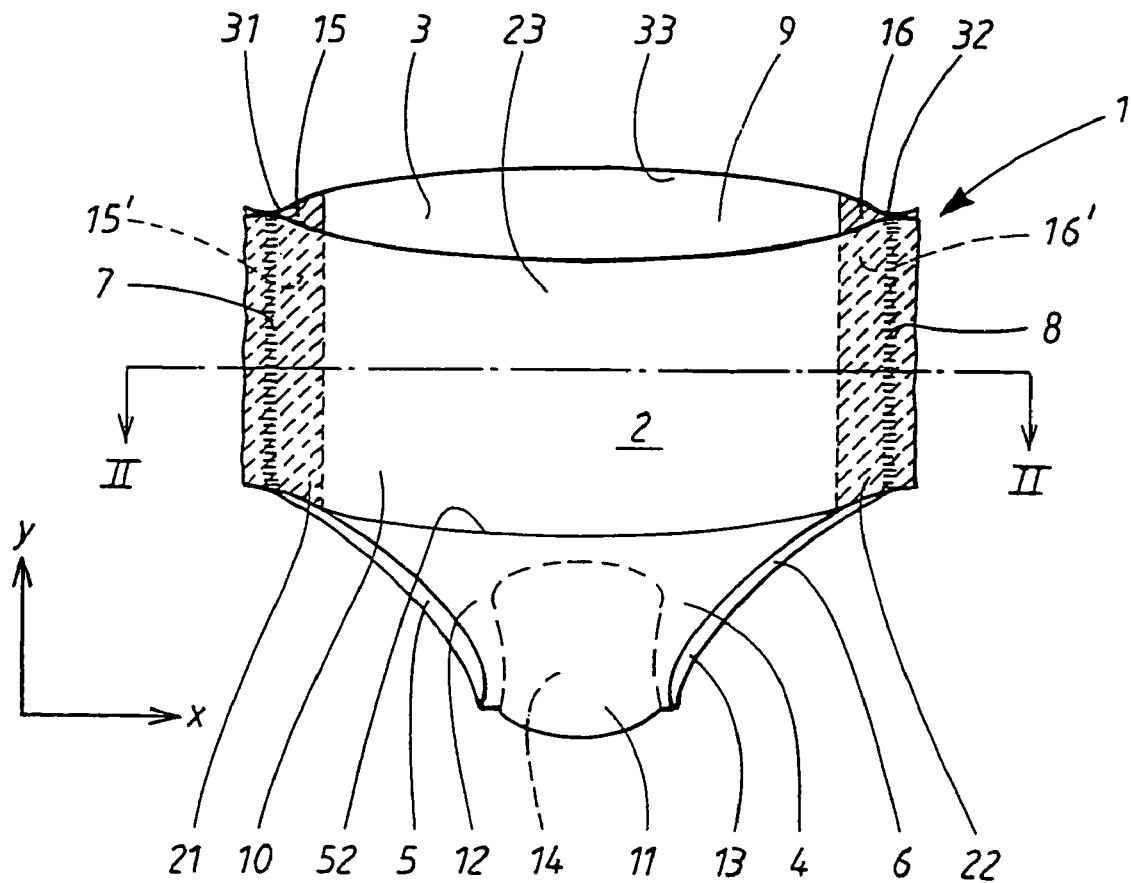
FIG. 1 shows a schematic perspective view of an illustrative embodiment of hygiene pants as described herein.

FIG. 1 shows hygiene pants in the form of diaper pants 1 for children or incontinent adults. The diaper pants 1 have a front portion 2, a rear portion 3 and a crotch portion 4 at which leg openings 5, 6 are arranged. The diaper pants have a transverse direction, which in FIG. 1 has been marked with x, and a longitudinal direction, which has been marked with y. The outer longitudinal edge portions 21 and 22 of the front portion, as seen in the transverse direction, are connected by weld seams 7 and 8 to the outer longitudinal edge portions 31 and 32 of the rear portion 3, as seen in the transverse direction, in order to form a waist opening 9, which is delimited by the outer transverse edge portions 23 and 33 of the front portion and rear portion.

The hygiene pants include an outer cover 10. The cover 10 is preferably elastic, and may comprise an elastic laminate containing an elastic film applied between two nonwoven layers. Three-layer elastic laminates suitable for the purpose are described in detail, for example, in PCT applications WO 2005/122984 and WO 2005/122985. A suitable two layer elastic laminate is described in PCT Patent Applications PCT/SE2006/000563 and PCT/SE2006/000564.

Reference is made to the entire content of these patent applications, both as regards examples of suitable materials for the diaper pants and also as regards illustrative embodiments of the described diaper pants. PCT Patent Applications PCT/SE2006/000563 and PCT/SE2006/000564, and publications WO 2005/122984 and WO 2005/122985 are accordingly incorporated herein in their entirety to the extent that the descriptions therein are not inconsistent with descriptions herein.

The laminate is elastic at least in the transverse direction of the diaper pants, that is, in the x direction in FIG. 1. The elasticity in the x direction is preferably at least 30%, more preferably at least 50%, and most preferably at least 70%, measured according to the elasticity test described in the abovementioned patent applications.

The outer fiber layers in the laminate can provide softness and a textile feel. Examples of suitable materials are meltblown nonwovens and spunbond nonwovens. The grammage of said fibrous layers is preferably between 10 and 35 g/m², preferably between 12 and 30 g/m², and particularly preferably between 15 and 25 g/m². Examples of suitable fiber materials such as polyethylene and polypropylene are indicated in the abovementioned patent applications. The elastic film is expediently perforated so that the cover is made permeable to air and vapour. The grammage of the elastic film is expediently between 20 and 100 g/m², preferably between 20 and 60 g/m². Suitable examples of materials and material combinations for the elastic film are indicated in abovementioned patent applications WO 2005/122984 and WO 2005/122985.

Laminate in the cover 10 can be produced according to a modified version of the method disclosed in WO 03/047488. As has been described in said patent applications WO 2005/122984 and WO 2005/122985, the modification is that at least one of the non-elastic nonwoven layers has been stretched under maximum load so that significant strength is still present in at least one of the nonwoven layers.

In other embodiments, materials such as those described in PCT Patent Applications PCT/SE2006/000563 and PCT/SE2006/000564 can be used in constructing the cover. Elastic panels as described therein are formed by preparing a two-layer laminate comprising a non-elastic fibrous nonwoven web and an elastic film. Suitable materials for such laminates are described therein. The two layer laminate is activated by stretching in at least one direction by 10 200% to render the laminate elastic in at least that direction. In a pant-forming process, stretched laminate can be laminated to another chassis component web.

Alternatively, the laminate for the cover can also be composed of an elastic laminate which has been produced entirely in accordance with what is described in WO 03/047488. Reference is made to the entire content of this patent publication, both as regards examples of suitable materials for the diaper pants and also as regards illustrative embodiments of the described diaper pants. Accordingly, WO 03/047488 is incorporated herein in its entirety to the extent that the descriptions therein are not inconsistent with descriptions herein.

The term "cover" used herein designates a framework that supports the pants and preferably elastically surrounds a user's trunk, thereby supporting the pants as a whole. In the illustrative embodiment shown in FIG. 1, the cover is composed of a front portion 2 and a rear portion 3. The diaper pants according to FIG. 1 have a crotch portion 4 welded to the cover and in the form of an absorption unit 11. This absorption unit 11 has an outer liquid-tight sheet 12, an inner liquid-permeable sheet 13, and an absorption body 14 arranged between these sheets. The liquid-permeable sheet can, for example, be composed of a nonwoven, such as a spunbond. The outer liquid-tight sheet 12 can, for example, be composed of a thin plastic film, such as a film of polyethylene or polypropylene. The absorption body can, for example, be composed of fluff pulp of cellulose or absorbent foam, possibly in combination with superabsorbent material. Other suitable materials and material combinations for the liquid-tight sheet 12, the absorption body 14 and the liquid-permeable sheet 13 are set out in patent applications WO 2005/122984 and WO 2005/122985.

Hygiene pants as described in WO 03/047488 and the hygiene pants as described in patent publications WO 2005/122984 and WO 2005/122985 and PCT Patent Application PCT/SE2006/000563 comprise elastic laminates with a degree of elasticity suitable for use in hygiene pants. This has been achieved by partially or completely breaking fibers or bonds in at least one of the nonwoven layers surrounding the elastic films in the elastic laminate. A disadvantage of the nonwoven bonds in the laminate having been partially or completely broken is that the tensile strength of weld seams 7 and 8 is weakened by comparison to traditional diaper pants that comprise four bonded nonwoven layers connected by means of the weld seams.

Bonded nonwoven layers here designate nonwovens which have not been broken open or weakened during production of the cover, but which instead retain their tensile strength. In traditional diaper pants, the covers are composed of double nonwovens and of elastic threads lying between them. In the weld seams, therefore, there are no less than four layers of bonded nonwovens, thus providing a sufficiently strong weld seam.

Hygiene pants are subjected to considerable stresses when being put on. The hygiene pants are stretched and the weld seams are exposed to considerable stresses. Especially critical areas are the ends of the weld seams at the leg openings or the waist.

Figure 2:
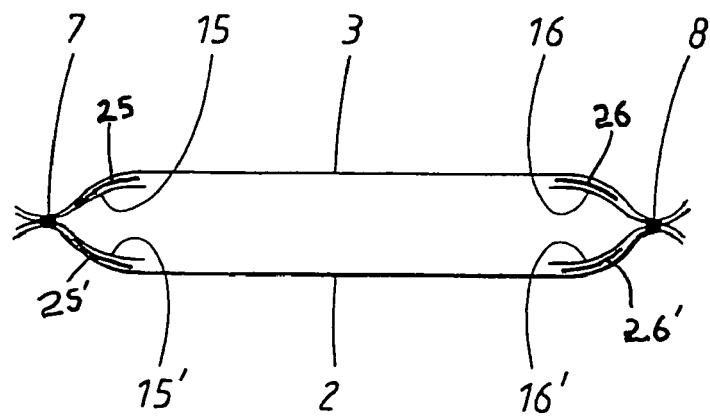
FIG. 2 shows a cross section along line II-II in FIG. 1.

In the embodiment according to FIG. 1, the weld seams 7 and 8 have been reinforced with reinforcing material strips 15, 15' and 16, 16', which nonwoven strips have been applied to the inside of the cover along the edge portions 21, 31 and 22, 32, as can be seen in FIG. 2. Preferably, reinforcing nonwoven strips 15 and 16 are adhesively affixed to rear portion 3 at adhesive locations 25, 26 proximate to welds 7, 8 but not in the areas of welds 7,8 and reinforcing nonwoven strips 15', 16' are adhesively affixed to front portion 2 at adhesive locations 25', 26' proximate to welds 7,8 but not in the areas of welds 7,8.

The reinforcing strips contain thermoplastic fibers, which, upon welding of the weld seams, reinforce the seam. Nonwoven materials are preferred. For example, meltblown materials and spunbond materials are suitable reinforcing materials. However, other flexible and optionally extensible materials may be used, for example Spunbond-Meltblown-Spunbond (SMS) laminates.

In alternative embodiments, it can be sufficient to include only pieces 15,16 or pieces 15',16' on either the back or front portions of the pants. Where the welds 7,8 are formed in diaper pants moving in a transverse direction and using a stationary ultrasonic horn and a transversely moving anvil, it is preferable to include at least pieces 5,16 or 15',16' affixed to whichever of the front or back portions are disposed toward the stationary horn as the weld is formed.

The reinforcing strips 15,16 can, for example, be made of spunbond or meltblown nonwoven and are applied to the edge portions of the cover before these are welded together. As stated, the strips are preferably adhesively attached to the cover at the time the strips are applied. The reinforcing strips are preferably not stretched; thus that the fiber bonds have not been weakened on application to the edge portions of the cover. When the edge portions are welded together, the reinforcing strips can retain substantially all of their tensile strength, in contrast to fiber layers of elastic material in which the fiber bonds have been partially or completely broken.

The presence of the reinforcing strips in the welds can provide reinforcement of the bond between the cover layers. In addition, by adhesively affixing the reinforcing strip to an inner surface of the cover material at a region proximate to the weld, the reinforcing strip can provide a redundant connection. If the welded bond formed between an elastic cover portion and a reinforcing strip fails as a result of weakened or broken fiber bonds in the elastic cover material, the adhesive attaching the reinforcing strip to the elastic cover can maintain the integrity of the seam.

This is because, the welded bond between reinforcing strips and/or between a reinforcing strip and a cover portion that is disposed towards an anvil that is moving transversely with the hygiene pant as a when a longitudinal ultrasonic weld seam is formed at the transverse edges of transversely moving hygiene pants tends to be stronger than the bond between two directly welded elastic cover sheets or an elastic cover sheet and a reinforcing strip that is disposed towards a stationary horn when a longitudinal ultrasonic weld seam is formed at the transverse edges of transversely moving hygiene pants.

Figure 3:
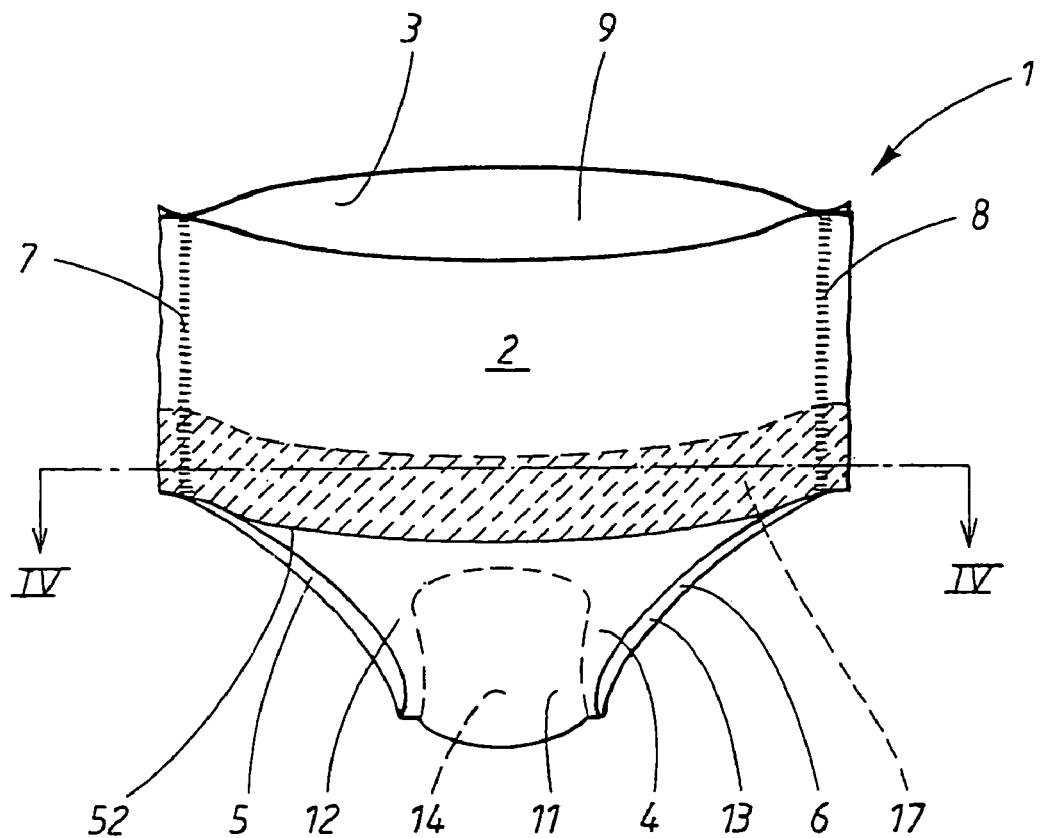
FIG. 3 shows a schematic perspective view of another illustrative embodiment of hygiene pants as described herein.
Figure 4:
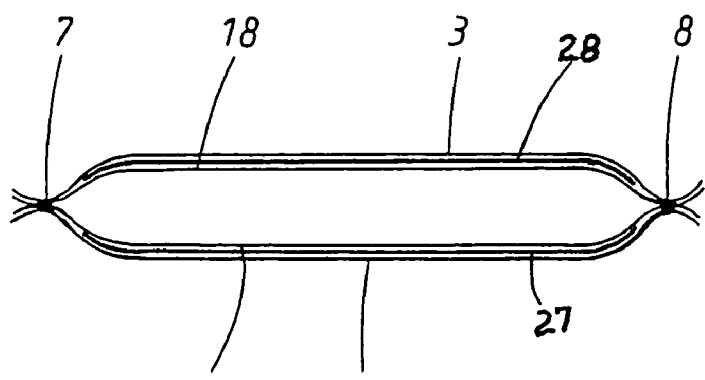
FIG. 4 shows a cross section along line IV-IV in FIG. 3.

As has been mentioned above, the stresses on the weld seams are considerable at the leg openings. In the embodiment shown in FIGS. 3 and 4, two reinforcing strips 17, 18 have been applied to the inside of the cover across the hygiene pants and only across the inner end portions of the end portions of the cover, i.e. at the leg openings. The reinforcing strips 17, 18 are applied, one on the front portion and one on the rear portion, before these portions have been welded together by means of the weld seams to form the cover. Preferably, strips 17, 18 are adhesively affixed to back and front portions 3, 2 by adhesive 27, 28, which is applied at least proximate to the areas of welds 7, 8, but not in the area where the weld is formed. In FIGS. 3 and 4, the details corresponding to equivalent details in the illustrative embodiment in FIG. 1 have been provided with the same reference numbers.

Figure 5:
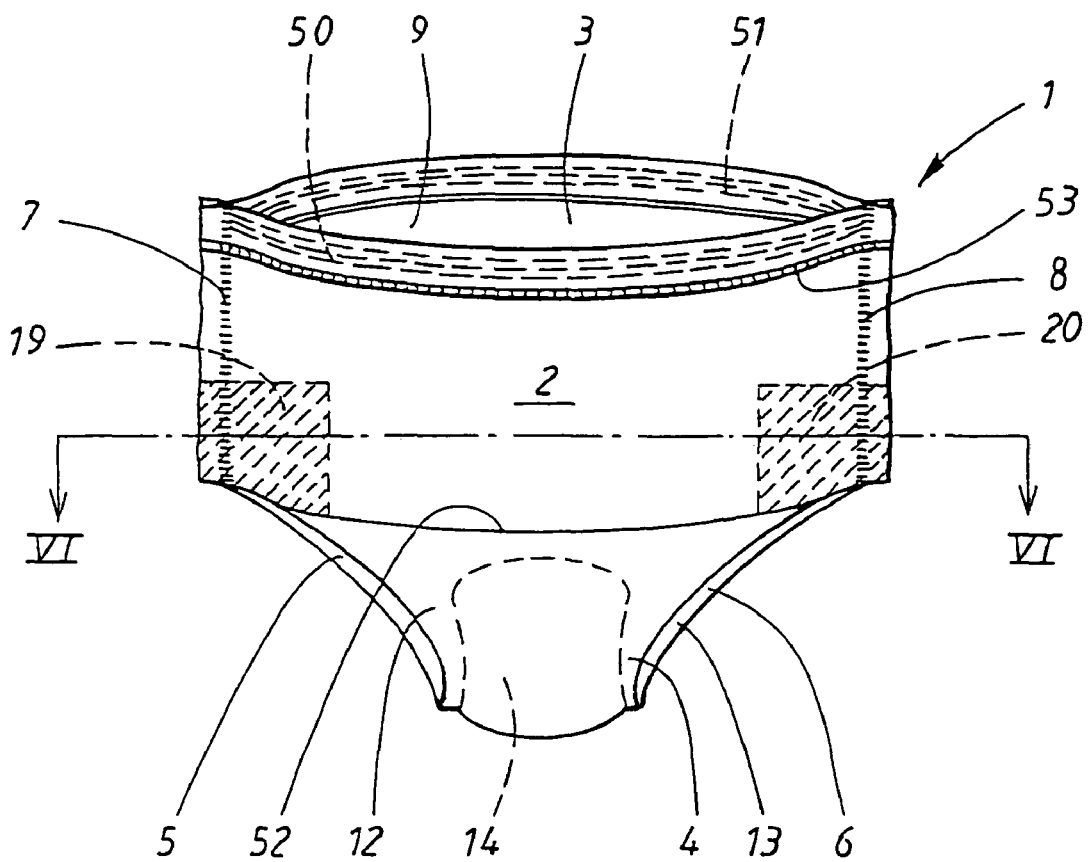
FIG. 5 shows a schematic perspective view of another illustrative embodiment of hygiene pants as described herein.
Figure 6:
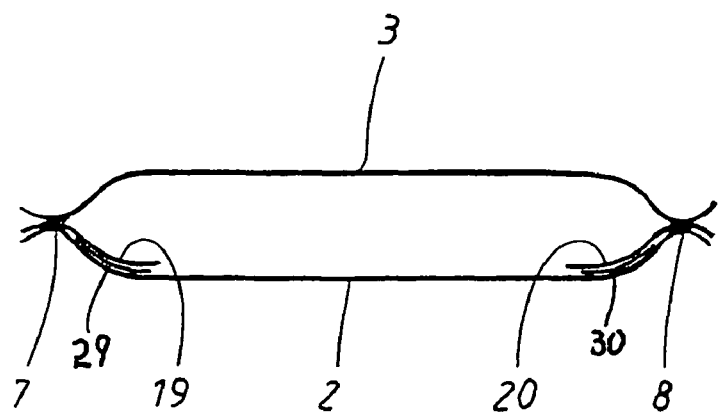
FIG. 6 shows a cross section along line VI-VI in FIG. 5.

FIGS. 5 and 6 show diaper pants where only the edge portions of the cover in immediate proximity to the leg openings have been reinforced with reinforcing strips 19 and 20. In this embodiment, only one strip has been applied inside the front portion 2 of the cover at the leg opening. In an alternative not shown, strips 19, 20 could be applied to back portion 3. Where the weld seams 7,8 are formed in transversely moving pants by using a stationary ultrasonic horn and a transversely moving anvil, it is preferable that strips 19, 20 are adhesively affixed to whichever of the front or back portion of the pant is disposed toward the stationary horn. In FIGS. 5 and 6, the details corresponding to equivalent details in the embodiment according to FIGS. 1 and 2 have been provided with the same reference numbers.

In the embodiment according to FIG. 5, the front portion and rear portion of the hygiene pants have been provided with elastic waist bands 50 and 51. These waist bands can expediently be composed of two nonwoven layers with a number of elastic threads applied between the nonwoven layers. The waist bands are connected to the front portion and the rear portion by means of transverse weld joins of which one 53 has been indicated in FIG. 5. When welding together the front portion and rear portion, the waist bands 50 and 51 are welded together by means of the weld seams 7 and 8. By means of the arrangement of the waist bands, the weld seams 7 and 8 are reinforced in the critical portions nearest to the waist opening. In preferred embodiments, the attachment of the nonwoven layers of the waist bands to the front and back portions of the cover using glue applied longitudinally and proximate to the welds 7,8.

Figure 7:
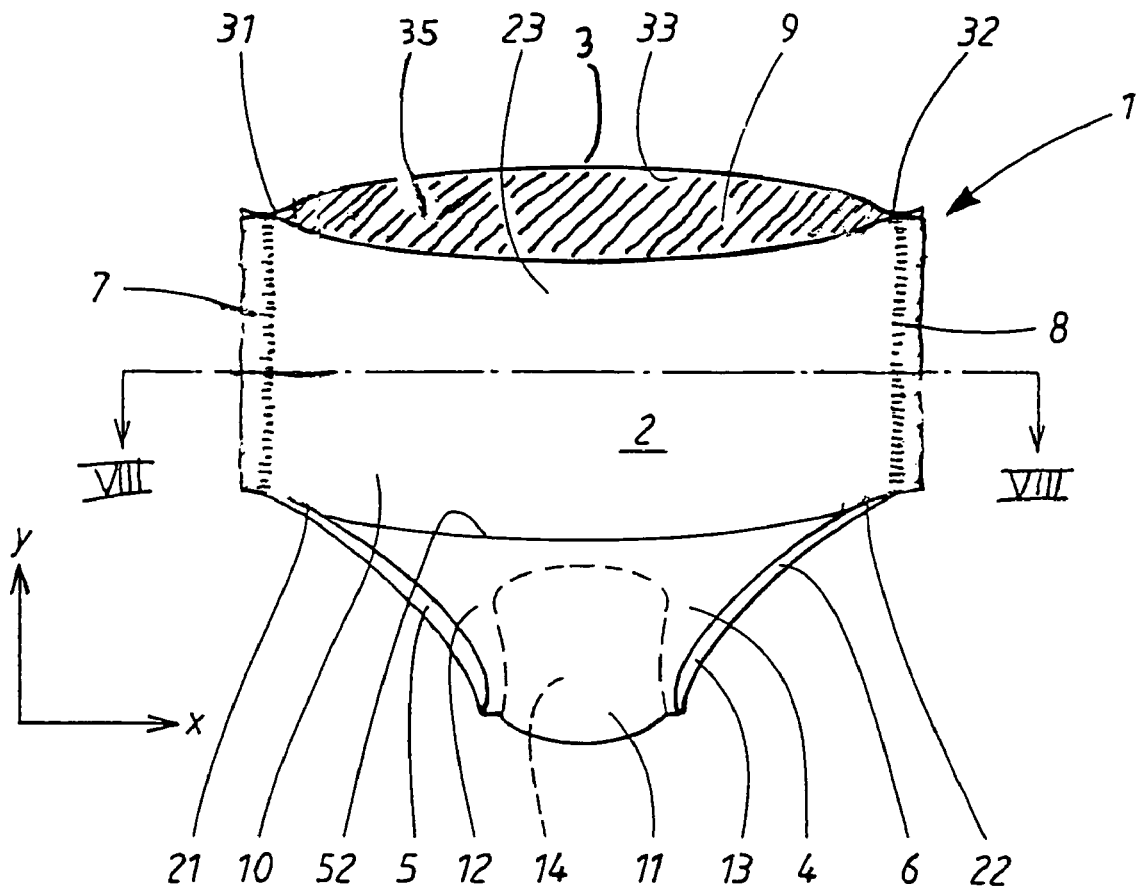
FIG. 7 shows a schematic perspective view of another illustrative embodiment of hygiene pants as described herein.
Figure 8:
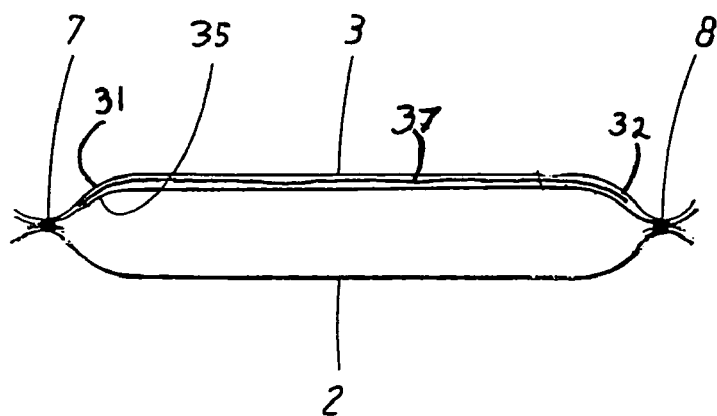
FIG. 8 shows a cross section along line VIII-VIII in FIG. 7.

FIGS. 7 and 8 show diaper pants in which reinforcing material 35 is applied across the width of the back portion. The reinforcing material 35 preferably extends in the longitudinal direction for substantially the length of welds 7,8. A reinforcing web, such as a bonded nonwoven web, laminated to the elastic panel may serve as both a cover layer and a reinforcing material, which is preferred when the cover is constructed using a two-layer elastic laminate such as described in PCT Patent Applications PCT/SE2006/000563 and PCT/SE2006/000564. The reinforcing material is preferably adhesively affixed to an inside surface of the elastic laminate cover while the cover is in a transversely extended state, for example the elastic laminate panel may be extended in the transverse direction about 10% to 200% preferably about 20% to about 125%, more preferably about 50% to about 70% at the tiem the laminate and reinforcing material are affixed.

In the illustrated embodiment, only one piece of reinforcing material has been applied inside the back portion 3 of the cover. In an alternative not shown, a single piece of reinforcing material could be applied to front portion 2. Reinforcing strips that do not extend transversely across the width of the pant may be combined with reinforcing material that does extend across the width of the pant.

Where the weld seams 7,8 are formed in transversely moving pants by using a stationary ultrasonic horn and a transversely moving or rotating anvil, it is preferable that reinforcing material 35 is adhesively affixed to whichever of the front or back portion of the pant is disposed toward the stationary horn. Alternatively, pieces of reinforcing material may be applied to both the front and back portions. In FIGS. 7 and 8, the details corresponding to equivalent details in the embodiment according to FIGS. 1 and 2 have been provided with the same reference numbers.

In the illustrative embodiments described above, the cover comprises front and rear portions and a separate crotch portion that has been welded to the rest of the cover by means of a weld which has been indicated by 52 in the drawings. Thus, in various exemplary embodiments, the cover may be made of one piece of elastic laminate or of separate pieces of material with some pieces being substantially non-elastic. The diaper pants according to FIGS. 1-8 are illustrated with a crotch portion which is substantially non-elastic under the application stresses.

Alternatively, the cover can also comprise the crotch portion, i.e. so that front portion, rear portion and crotch portion are in one piece of elastic material. The absorption unit is applied in this case in the crotch portion inside the cover and connected to the latter, for example by means of melt adhesive.

Figure 9:
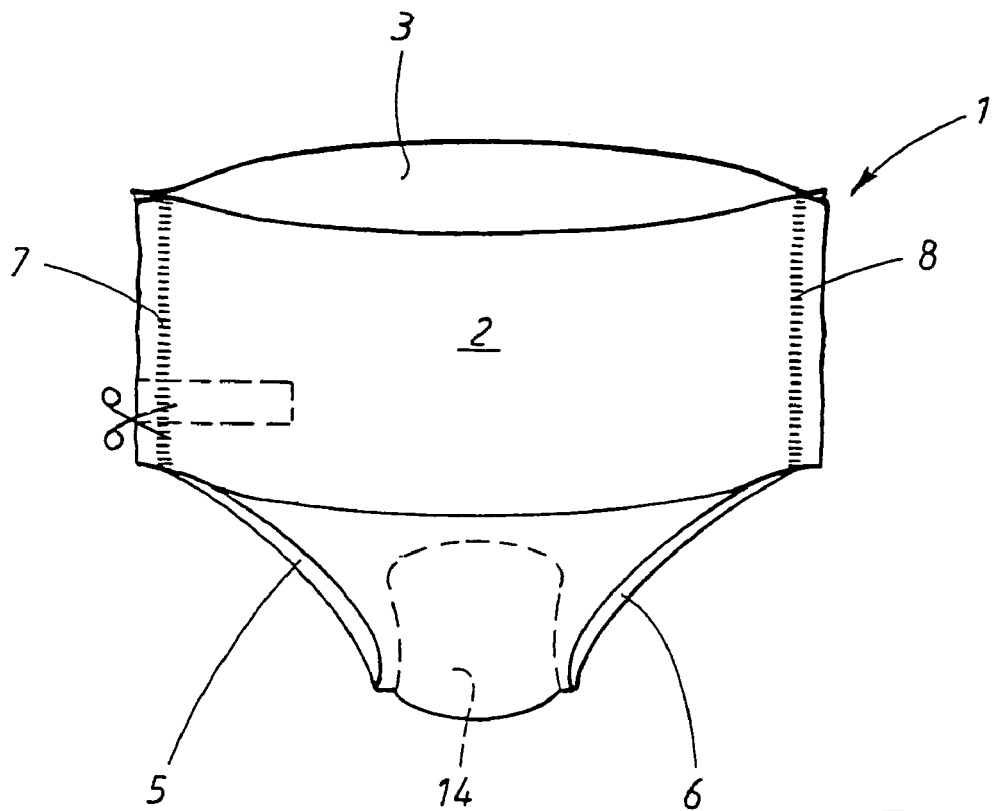
FIGS. 9-11 show, schematically, a method for measuring the weld strength of the hygiene pants according to a preferred embodiment.
Figure 10:
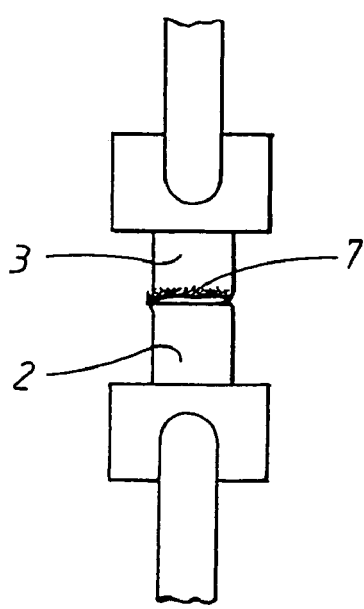
Figure 11:
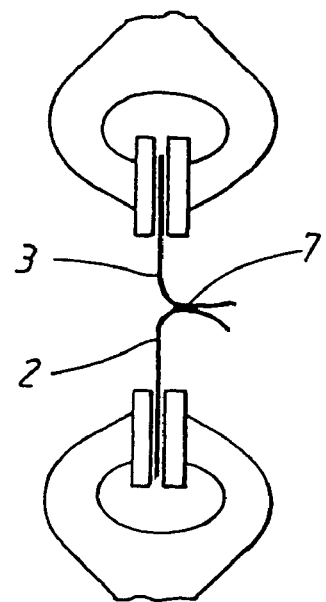

The tensile strength of the weld seams is measured according to the method (reference ASTM D 882) described in patent application WO 2005/122984. Test specimens are cut from the products, as shown in FIG. 9, in areas which are reinforced with reinforcing strips. The width of the test specimens will be 25.4 mm and the length if possible 50 mm longer than the distance between the clamps on the tensile test instrument Instron 4301. FIGS. 10 and 11 show how the test specimens are secured in the clamps.

To illustrate the effect of the reinforcement of the weld seams by means of nonwoven strips, Tables 1 and 2 show test results for measurements of the tensile strength of a weld seam for connecting two layers of an elastic laminate with and without reinforcement by nonwoven strips in various configurations. Table 1 provides a comparison of results obtained without reinforcing strips versus using reinforcing strips that are not adhesively affixed to the elastic laminate cover. Table 2 shows results that can be obtained using reinforcing strips with and without adhesively affixing one reinforcing strip to the elastic laminate cover at a location proximate to each weld, but not in the welded area. Table 2 further provides comparisons of higher basis weight reinforcing strip materials and the combination of a strip that is not adhesively affixed with a strip that is adhesively affixed.

The elastic laminate used in the test specimens comprises an inner elastomeric, three-ply film of PE-SEBS-PE provided with holes and having a grammage of 36 g/m$^2$ and two outer sheets of spunbond nonwoven, polypropylene, which each have a grammage of 22 g/m$^2$. The laminate has been produced according to a modified version of the method described in WO 03/04788. According to the modified version, a spunbond sheet is applied to the film in a tacky state and thus binds to the film, while the other spunbond sheet is adhesively laminated to the film by use of, for example, a pressure-sensitive adhesive (adhesive quantity 3 g/m$^2$). The laminate is stretched gradually until the non-elastic spunbond sheets are stretched to a point less than to the extension at maximum loading in order to maintain some of their strength in the spunbond layers.

The grammages of the layers described above concerns the finished material after stretching. Before stretching, the grammages for the individual layers were: inner film 40 g/m$^2$, outer spun bond layer 25 g/m$^2$, and adhesive layer 3 g/m$^2$. Since it is difficult to measure the grammages for individual layers after lamination and stretching, an approximation has been made on the basis of the grammages of the layers before lamination and stretching. The total grammage for the laminate before stretching was 93 g/m$^2$ and after stretching the grammage was 85 g/m$^2$, which corresponds to a deformation of about 10% it has been assumed that the deformation of the individual fiber layers and the film is identical, i.e. about 10%.

The reinforcing nonwoven strips were made of spunbond with a grammage of 20 g/m$^2$ in Table 1 and 20 g/m$^2$ or 30 g/m$^2$ in Table 2. As will be seen from Table 1, the tensile strength for the reinforced weld was on average 10 N/25.4 mm$^2$ greater than the weld consisting of only two elastic laminates. As will be seen from Table 2, gluing a reinforcing strip to the laminate at the back portion, which in this example is the portion that is disposed toward a stationary horn as the weld is formed using a transversely rotating anvil and a stationary horn, can provide further reinforcement.

Figure 12:
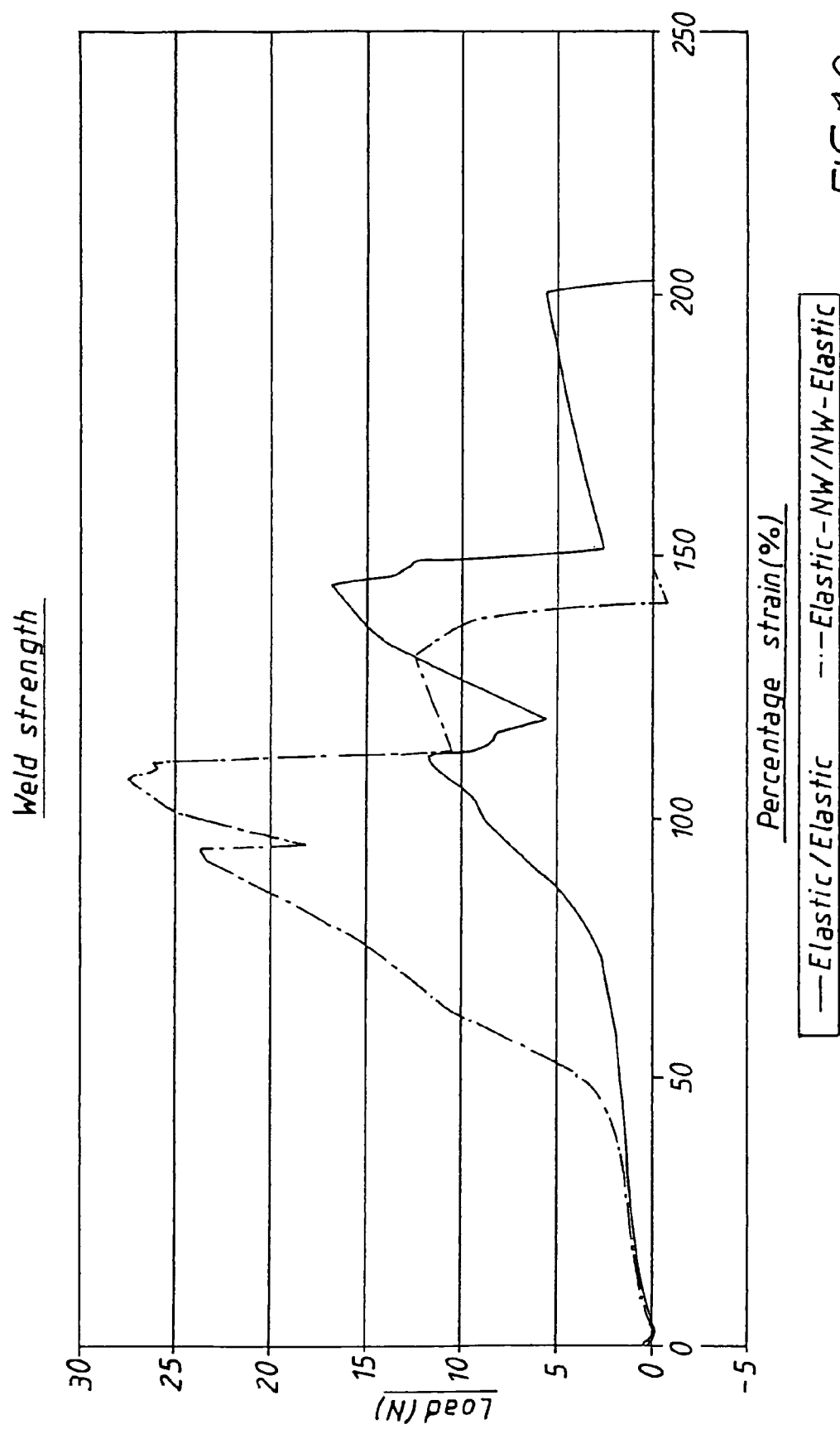
FIG. 12 shows a strain/load diagram to illustrate the change in weld strength with a reinforcement as described herein.

The particular values reflected in each table are of course due to the particular construction of the layers and the grammage. The welding method, bonder force setting, amplitude setting, and weld pattern also affect the strength. Therefore, Table 1 should not be directly compared with Table 2. However, the results shown in Table 1 illustrates clearly that a substantial reinforcement of the weld seam can be obtained with the aid of reinforcing nonwoven strips. The results shown in Table 2 show that further reinforcement of the weld seams can be obtained by adhesively affixing at least one reinforcing strip. FIG. 12 shows the stress-strain diagram for the test that corresponds to the results in Table 1.

TABLE 1

Tensile strength of welds formed between elastic laminates with and without reinforcing nonwoven strips.

| | Elastic/Elastic (no reinforcement) | | | Elastic-NW/NW-Elastic (two reinforcing strips - no glue) | |
|---|---|---|---|---|---|
| Sample | Maximum Force (N) | Elongation at Max Load (%) | Sample | Maximum Force (N) | Elongation at Max Load (%) |
| 1 | 16.81 | 145 | 1 | 19.38 | 78 |
| 2 | 15.65 | 108 | 2 | 33.63 | 109 |
| 3 | 16.12 | 118 | 3 | 21.26 | 91 |
| 4 | 13.83 | 117 | 4 | 29.17 | 100 |
| 5 | 12.89 | 114 | 5 | 24.70 | 99 |
| 6 | 15.46 | 112 | 6 | 28.23 | 108 |
| 7 | 16.42 | 109 | 7 | 21.49 | 93 |
| 8 | 17.99 | 107 | 8 | 31.56 | 110 |
| 9 | 22.11 | 117 | 9 | 27.57 | 108 |
| 10 | 17.96 | 110 | 10 | 30.58 | 108 |
| AVG | 16.52 | 116 | AVG | 26.76 | 100 |
| SD | 2.54 | 11 | SD | 4.83 | 10 |
| MIN | 12.89 | 107 | MIN | 19.38 | 78 |
| MAX | 22.11 | 145 | MAX | 33.63 | 110 |

TABLE 2

Tensile strength of reinforced welds formed between elastic laminates with and without adhesively affixing a reinforcing nonwoven strip to an elastic laminate layer.

| | No Glue | | | | Strip Glued on Back Portion | |
|---|---|---|---|---|---|---|
| | 1 strip 20 g/m$^2$ | 2 strips 20 g/m$^2$ | 2 strips 30 g/m$^2$ | 20 g/m$^2$ | 20 g/m$^2$ + 20 g/m$^2$ on front without glue | 30 g/m$^2$ + 30 g/m$^2$ on front without glue |
| AVG Right | 12.95 | 11.27 | 11.00 | 18.50 | 21.40 | 24.60 |
| SD Right | 1.50 | 1.05 | 1.31 | 1.90 | 3.00 | 3.10 |

TABLE 2-continued

Tensile strength of reinforced welds formed between elastic laminates with and without adhesively affixing a reinforcing nonwoven strip to an elastic laminate layer.

|  | No Glue | | | | Strip Glued on Back Portion | |
|---|---|---|---|---|---|---|
|  | | | | | 20 g/m² + 20 g/m² on front | 30 g/m² + 30 g/m² on front |
|  | 1 strip 20 g/m² | 2 strips 20 g/m² | 2 strips 30 g/m² | 20 g/m² | without glue | without glue |
| MIN Right | 10.00 | 8.50 | 8.70 | 14.80 | 16.00 | 18.30 |
| AVG Left | 13.33 | 12.56 | 12.70 | 16.50 | 22.80 | 23.70 |
| SD Left | 2.57 | 1.66 | 1.70 | 1.90 | 2.50 | 2.90 |
| MIN Left | 8.70 | 9.5 | 10.50 | 12.20 | 18.50 | 18.10 |

Practical tests have shown that the tensile strength of the weld seams in a direction transverse to the weld seam should be at least 5 N/25.4 mm, preferably 7 N/25.4 mm or more preferably at least 9 N/25.4 mm to ensure that diaper pants of reliable function are obtained. Across samples of 25 or more hygiene pants, minimum side seam strengths of at least 10 N/25.4 mm are preferred, or of at least 12 N/25.4 mm are more preferred, while average tensile strengths of at least 15 N/25.4 mm or 20 N/25.4 mm may also be preferred.

Hygiene pants when used should be able to be easily opened at the weld seams in order to make it easier to take them off. To obtain a reliable function in this respect, it is desirable that the breaking strength of the cover in the transverse direction exceeds the tensile strength for the reinforced weld seams so that the hygiene pants, when being taken off, do not fall apart in an uncontrolled manner and instead break at the seams. The fact that the reinforcements of the seams can be varied through the choice of nonwoven, the number of layers and the grammage of the reinforcement strips opens up a new possibility of varying the strength of the weld seam. This strength can also be varied through the choice of weld type and weld pattern.

FIGS. 13-15 illustrate a method of making a reinforced ultrasonic or thermally bonded weld seam where reinforcing material is adhesively attached to elastic laminate cover material proximate to the location of a weld between two layers of elastic laminate material. In FIG. 13, elastic laminate material 105, 106 move transversely in direction 111 under a stationary ultrasonic horn 101. Anvil 102 bearing weld patterns 104 is attached to the surface of roller 103 moving in direction 113. Reinforcing material 107 is attached the inner surface of elastic laminate 105, which is disposed towards the stationary horn, by adhesive glue 108. Glue 108 could extend the full length of reinforcing material 107, but it is preferable that glue 108 is positioned proximate to, but not at, the location where the weld will be formed. After welds are formed by compression of the laminates between horn 101 and weld patterns 104, the welded material is cut at line 110 to form a seam 112 as illustrated in FIG. 14. In practical experience, the weld 112 tends to be stronger on the anvil side. By use of this method, any weakness in the weld 112 on the horn side is reinforced by the use of glue 108 to affix reinforcing material 107 to the horn-side elastic laminate 105. FIG. 15 illustrates a seam formed by including an additional reinforcing material 107' on the anvil side elastic laminate 106, which can be applied with or without glue 108'.

The methods and hygiene pants described herein are not limited to the illustrative embodiments described above. Rather, a number of modifications are possible within the scope of the attached patent claims. For example, reinforcement strips can be applied outside two elastic materials which are to be welded together, either outside both laminates or in the form of a single strip outside one of the laminates.

An elasticized cover does not need to be made of elastic laminate across the whole front portion and whole rear portion, and instead parts of the front portion and/or rear portion can be made of inelastic material. It is preferred that the hygiene pants are sufficiently elastic so that the pants can be put on and taken off with ease. For example, it may suffice for the rear portion to be made of elastic laminate and for the rest of the hygiene pants to be non-elastic.

Alternatively, the hygiene pants as described herein can have covers in the form of elastic laminates only in the side portions of the front portion and rear portion, and otherwise have central non-elastic parts along the front portion, rear portion and crotch portion cover in the transverse direction exceeds the tensile strength for the reinforced weld seams.

What is claimed is:

1. A disposable hygiene pants having a longitudinal direction and a transverse direction, the hygiene pants comprising in the longitudinal direction, a front portion, an intermediate crotch portion provided with two leg cut outs, and a rear portion, the outer longitudinal edge portions of the front portion being connected by longitudinal weld seams to the outer longitudinal edge portions of the rear portion thereby forming a waist opening that is delimited by the outer transverse edge portions of the front portion and of the rear portion, and forming two leg openings that are outwardly delimited in the transverse direction by inner end portions of the weld seams, wherein the hygiene pants further comprise an outer cover comprising an elastic laminate comprising an elastic film applied between two nonwoven layers and the hygiene pants further comprise an absorption unit that extends in the longitudinal direction across at least part of the crotch portion, wherein said weld seams each comprise at least one piece of reinforcing bonded nonwoven material containing thermoplastic fibers wherein the at least one piece of reinforcing bonded nonwoven material is adhesively affixed to said longitudinal edge portions of the front portion or rear portion of the hygiene pants at an adhesive location proximate to the weld seam, wherein the tensile strength of the weld seams, in the transverse direction, exceeds 5 N/25.4 mm at least in the portions reinforced with said reinforcing bonded nonwoven material and wherein the breaking strength of said cover in the transverse direction exceeds the tensile strength for the reinforced weld seams, and wherein the elastic laminate is activated by stretching, and the reinforcing bonded nonwoven material is attached to the elastic laminate after the activation so that the reinforcing bonded nonwoven material has not been broken open or weakened, or stretched during the activation of the elastic laminate.

2. The hygiene pants according to claim 1, wherein at least one piece of reinforcing bonded nonwoven material is between each longitudinal edge portion of the front portion and rear portion of the cover.

3. The hygiene pants according to claim 2, wherein said reinforcing bonded nonwoven material extends along substantially the whole of each longitudinal edge.

4. The hygiene pants according to claim 2, wherein each weld seam is reinforced by a single piece of reinforcing bonded nonwoven material.

5. The hygiene pants according to claim 4, wherein said reinforcing material is a single piece of reinforcing bonded nonwoven material extending transversely across the hygiene pants.

6. The hygiene pants according to claim 5, wherein, in the longitudinal direction of the hygiene pants, said single transverse nonwoven strip extends only across said inner end portions of the two edge portions.

7. The hygiene pants according to claim 2, comprising reinforcing material on both the front portion and the rear portion, at least along the inner end portions of the longitudinal edge portions, such that the weld seams comprise two layers of the reinforcing material in the reinforced areas.

8. The hygiene pants according to claim 2, wherein the tensile strength across the weld seams in the reinforced portions exceeds 7 N/25.4 mm.

9. The hygiene pants according to claim 2, wherein the tensile strength across the weld seams in the reinforced portions exceeds 9 N/25.4 mm.

10. Hygiene pants according to claim 1, wherein the strength of the bond in said weld seams between either the front or the back portion and the reinforcing material is weaker than between the other of the front or the back portion and wherein the reinforcing material is adhesively affixed to the inner surface of whichever of the front or back portion is on the weaker side.

11. Hygiene pants according to claim 1, wherein the adhesive location does not extend into an area of the weld seam.

12. A disposable hygiene pants having a longitudinal direction and a transverse direction, the hygiene pants comprising in the longitudinal direction, a front portion, an intermediate crotch portion provided with two leg cut outs, and a rear portion, the outer longitudinal edge portions of the front portion being connected by longitudinal weld seams to the outer longitudinal edge portions of the rear portion thereby forming a waist opening that is delimited by the outer transverse edge portions of the front portion and of the rear portion, and forming two leg openings that are outwardly delimited in the transverse direction by inner end portions of the weld seams, wherein the hygiene pants further comprise an outer cover and an absorption unit that extends in the longitudinal direction across at least part of the crotch portion, wherein said weld seams each comprise at least one piece of reinforcing material containing thermoplastic fibers wherein the at least one piece of reinforcing bonded nonwoven material is adhesively affixed to the front portion or rear portion of the hygiene pants at an adhesive location proximate to the weld seam, wherein the tensile strength of the weld seams, in the transverse direction, exceeds 5 N/25.4 mm at least in the portions reinforced with said reinforcing material and wherein the breaking strength of said cover in the transverse direction exceeds the tensile strength for the reinforced weld seams, and wherein the adhesive location does not extend into an area of the weld seam.

13. The hygiene pants according to claim 12, wherein the cover comprises elasticized material.

14. The hygiene pants according to claim 13, wherein the cover comprises an elastic laminate comprising an elastic film applied to a layer of nonwoven material.

15. The hygiene pants according to claim 14, wherein the cover comprises an elastic laminate comprising an elastic film applied between two layers of nonwoven material.

16. The hygiene pants according to claim 12, wherein said reinforcing material extends along substantially the whole of each longitudinal edge.

17. The hygiene pants according to claim 12, wherein each weld seam is reinforced by a single piece of reinforcing material.

18. The hygiene pants according to claim 17, wherein said reinforcing material is a single piece of reinforcing material extending transversely across the hygiene pants.

19. The hygiene pants according to claim 18, wherein in the longitudinal direction of the hygiene pants, said single reinforcing material extends only across said inner end portions of the two edge portions.

20. The hygiene pants according to claim 18, comprising reinforcing material on both the front portion and the rear portion, wherein at least the reinforcing material on either the front portion or the rear portion is adhesively affixed at least in the longitudinal end portions thereof proximate to the weld seams, such that the weld seams comprise two layers of the reinforcing material in the reinforced areas, at least one of which is also adhesively affixed to a cover portion.

21. The hygiene pants according to claim 12, comprising reinforcing material on both the front portion and the rear portion, at least along the inner end portions of the longitudinal edge portions, such that the weld seams comprise two layers of the reinforcing material in the reinforced areas.

22. Hygiene pants according to claim 12, wherein the strength of the bond in said weld seams between either the front or the back portion and the reinforcing material is weaker than between the other of the front or the back portion and wherein the reinforcing material is adhesively affixed to the inner surface of whichever of the front or back portion is on the weaker side.

23. A disposable hygiene pants having a longitudinal direction and a transverse direction, the hygiene pants comprising in the longitudinal direction, a front portion, an intermediate crotch portion provided with two leg cut outs, and a rear portion, the outer longitudinal edge portions of the front portion being connected by longitudinal weld seams to the outer longitudinal edge portions of the rear portion thereby forming a waist opening that is delimited by the outer transverse edge portions of the front portion and of the rear portion, and forming two leg openings that are outwardly delimited in the transverse direction by inner end portions of the weld seams, wherein the hygiene pants further comprise an outer elastic cover and the hygiene pants further comprise an absorption unit that extends in the longitudinal direction across at least part of the crotch portion, wherein said weld seams each comprise at least one piece of reinforcing bonded nonwoven material containing thermoplastic fibers wherein the at least one piece of reinforcing bonded nonwoven material is adhesively affixed to an inner surface of each longitudinal edge portion of the front portion or rear portion of the hygiene pants at an adhesive location proximate to the weld seam, wherein the tensile strength of the weld seams, in the transverse direction, exceeds 5 N/25.4 mm at least in the portions reinforced with said reinforcing material and wherein the breaking strength of said cover in the transverse direction exceeds the tensile strength for the reinforced weld seams, and wherein the adhesive location does not extend into an area of the weld seam.

24. The hygiene pants according to claim 23, wherein the cover comprises an elastic laminate comprising an elastic film applied to a nonwoven layer.

25. The hygiene pants according to claim 24, wherein the cover comprises an elastic laminate comprising an elastic film applied between two nonwoven layers.

26. The hygiene pants according to claim 23, wherein the reinforcing material that is adhesively affixed to an inner surface of a longitudinal edge portion of the front portion or rear portion of the cover is affixed by glue that is applied proximate to, but not extending into, the area of the weld seam.

27. The hygiene pants according to claim 23, wherein said reinforcing material extends along substantially the whole of each longitudinal edge.

28. The hygiene pants according to claim 23, wherein each weld seam is reinforced by a single piece of reinforcing bonded nonwoven material.

29. The hygiene pants according to claim 28, wherein said reinforcing material is a single piece of reinforcing bonded nonwoven material extending transversely across the hygiene pants.

30. The hygiene pants according to claim 24, wherein in the longitudinal direction of the hygiene pants, said single transverse nonwoven strip extends only across said inner end portions of the two edge portions.

31. Hygiene pants according to claim 23, wherein the tensile strength across the weld seams in the reinforced portions exceeds 10 N/25.4 mm.

32. Hygiene pants according to claim 23, wherein the tensile strength across the weld seams in the reinforced portions exceeds 12 N/25.4 mm.

33. Hygiene pants according to claim 23, wherein the tensile strength across the weld seams in the reinforced portions exceeds 15 N/25.4 mm.

34. Hygiene pants according to claim 23, wherein the tensile strength across the weld seams in the reinforced portions exceeds 20 N/25.4 mm.

35. Hygiene pants according to claim 23, wherein the strength of the bond in said weld seams between either the front or the back portion and the reinforcing material is weaker than between the other of the front or the back portion and wherein the reinforcing material is adhesively affixed to the inner surface of whichever of the front or back portion is on the weaker side.

36. A disposable hygiene pants comprising an outer cover comprising an elastic laminate comprising an elastic film applied between two nonwoven layers,
the outer cover comprising in a longitudinal direction, a front portion, an intermediate crotch portion provided with two leg cut outs, and a rear portion,
the outer longitudinal edge portions of the front portion of the outer cover being connected to the outer longitudinal edge portions of the rear portion of the outer cover by longitudinal weld seams that each comprise at least one piece of reinforcing bonded nonwoven material containing thermoplastic fibers wherein the at least one piece of reinforcing bonded nonwoven material is adhesively affixed to said longitudinal edge portions of the front portion of the outer cover or rear portion of the outer cover of the hygiene pants at an adhesive location proximate to the weld seam,
thereby forming a waist opening that is delimited by the outer transverse edge portions of the front portion of the outer cover and of the rear portion of the outer cover, and forming two leg openings that are outwardly delimited in the transverse direction by inner end portions of the weld seams,
the hygiene pants further comprising an absorption unit that extends in the longitudinal direction across at least part of the crotch portion inside of the outer cover,
wherein the tensile strength of the weld seams, in the transverse direction, exceeds 5 N/25.4 mm at least in the portions reinforced with said reinforcing bonded nonwoven material and wherein the breaking strength of said cover in the transverse direction exceeds the tensile strength for the reinforced weld seams, and
wherein the elastic laminate is activated by stretching, and the reinforcing bonded nonwoven material is attached to the elastic laminate after the activation so that the reinforcing bonded nonwoven material has not been broken open or weakened, or stretched during the activation of the elastic laminate.

37. Hygiene pants according to claim 36, wherein the adhesive location does not extend into an area of the weld seam.

* * * * *